United States Patent [19]

Fujimura et al.

[11] Patent Number: 4,518,712
[45] Date of Patent: May 21, 1985

[54] PIPERAZINE DERIVATIVE AND ANALGESIC COMPOSITION CONTAINING THE SAME

[75] Inventors: Hajime Fujimura, Kyoto; Yasuzo Hiramatsu, Otsu; Tomio Yamazaki, Tokushima; Shozo Yamada, Tokushima; Takaji Honna, Tokushima, all of Japan

[73] Assignee: Taiho Pharmaceutical Company Limited, Tokyo, Japan

[21] Appl. No.: 275,690

[22] Filed: Jun. 22, 1981

[30] Foreign Application Priority Data

Jun. 30, 1980 [JP] Japan ................................ 55-89782
May 8, 1981 [JP] Japan ................................ 56-69689

[51] Int. Cl.³ .............................................. A01N 43/48
[52] U.S. Cl. .................................. 514/255; 544/392; 544/395
[58] Field of Search .................. 544/392, 395; 424/250

[56] References Cited

U.S. PATENT DOCUMENTS 2,830,056  4/1958  Ruschig et al. ...................... 544/392
3,037,024  5/1962  Parcell ................................. 544/392
3,394,137  7/1968  Morris ................................. 544/392
3,402,039  9/1968  Mussell et al. ...................... 544/392
3,506,666  4/1970  Morris ................................. 544/392

FOREIGN PATENT DOCUMENTS 2800954  7/1978  Fed. Rep. of Germany ...... 544/393

OTHER PUBLICATIONS

Irwin, et al., "J. Med. Chem.", vol. 15 (6), 1972, pp. 690–692.
"Chemical Abstracts", vol. 67, 1967, col. 43819z.
Prasad, et al., "Chemical Abstracts", vol. 70, 1969, col. 11676w.
Berberian, et al., "Chemical Abstracts", vol. 71, col. 29130u.
Irwin, et al., "Chemical Abstracts", vol. 77, 1972, col. 56687m.
Khanna, et al., "Chemical Abstracts", vol. 84, 1976, col. 4904e.
Fujimura, et al., "Chemical Abstracts", vol. 96, 1982, col. 199735d.
Robba, et al., "Chemical Abstracts", vol. 97, 1982, col. 127659e.

Primary Examiner—Glennon H. Hollrah
Assistant Examiner—James H. Turnipseed
Attorney, Agent, or Firm—Murray, Whisenhunt and Ferguson

[57] ABSTRACT

An analgesic composition containing as active ingredient a piperazine derivative represented by the general formula (1)

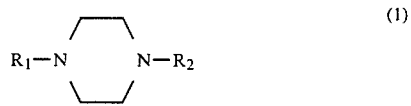

wherein $R_1$ represents a cyclopropylmethyl group, an isopropyl group or an allyl group and $R_2$ represents a phenyl group having as substituent a halogen atom or a trifluoromethyl group.

20 Claims, No Drawings

PIPERAZINE DERIVATIVE AND ANALGESIC COMPOSITION CONTAINING THE SAME

This invention relates to novel piperazine derivatives and, more particularly, to novel piperazine derivatives, processes for their preparation and analgesic compositions containing them as active ingredients.

The piperazine derivative of this invention is represented by the general formula (1):

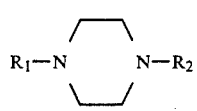

(1)

wherein $R_1$ represents a cyclopropylmethyl group, isopropyl group or allyl group and $R_2$ represents a phenyl group having as substituent a halogen atom or trifluoromethyl group. In the formula the halogen atom may be chlorine, bromine or fluorine atom.

The novel piperazine derivative of this invention may be in the form of addition salt with acids including inorganic acids such as, for example, hydrochloric acid, hydrobromic acid, sulfuric acid, nitric acid, phosphoric acid and boric acid, and organic acids such as, for example, oxalic acid, citric acid, acetic acid, lactic acid, tartaric acid, succinic acid, fumaric acid, and maleic acid.

The piperazine derivatives of this invention are novel compounds which have not been described in the literature, have an analgesic activity and are useful as analgesics.

The piperazine derivative (1) of this invention is prepared by the methods as exemplified below.

METHOD A

This method is characterized by allowing the halogen compound represented by the general formula (2) and the piperazine derivative represented by the general formula (3) according to the following reaction scheme:

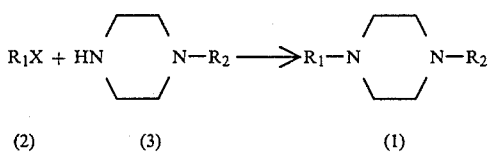

wherein $R_1$ and $R_2$ are as defined above and X represents a halogen atom.

The reaction between the halogenated compound (2) and the piperazine derivative (3) is conducted in a solvent and in the presence of a basic compound such as, for example, sodium hydroxide, potassium hydroxide, sodium carbonate, potassium carbonate, sodium bicarbonate, potassium bicarbonate, triethylamine, pyridine, or N,N-dimethylaniline. The solvent may be any of the inert organic solvents, being subject to no specific restriction. Examples of suitable solvents for use include benzene, toluene, xylene, methanol, ethanol, isopropanol, ether, dioxane, tetrahydrofuran, chloroform, dichloromethane, dichloroethane, and N,N-dimethylformamide.

The proportion of halogenated compound (2), piperazine derivative (3) and basic compound should be suitably selected, but it is generally advantageous to use in approximately equimolar amounts. The reaction temperature should also be suitably selected, but the reaction generally proceeds advantageously at a temperature from room temperature to the boiling point of the solvent.

METHOD B

This method is characterized by reducing an acylpiperazine derivative represented by the general formula (4) according to the following reaction scheme:

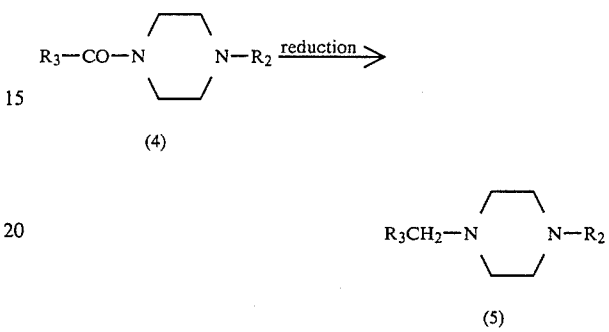

wherein $R_2$ is as defined above and $R_3$ represents a cyclopropyl group or vinyl group. The reduction of the acylpiperazine derivative (4) is carried out preferably in a solvent and in the presence of lithium aluminum hydride or diborane as reducing agent. The solvent should be an inert organic solvent which will not participate in the reaction; diethyl ether, tetrahydrofuran or diglyme are preferably used. The amount to be used of the reducing agent should be suitably selected; it is generally advantageous to use about 0.5 to about 5 moles of the reducing agent per mole of an acylpiperazine derivative (4). The reaction temperature should also be suitably selected; the reaction proceeds advantageously generally at a temperature from room temperature to around the boiling point of the solvent.

The acylpiperazine derivatives (4) used as the starting material in the above reaction are all novel compounds not described in the literature. They are obtained by the condensation of a carboxylic acid represented by the general formula (6) or a reactive derivative thereof with a piperazine derivative represented by the general formula (3).

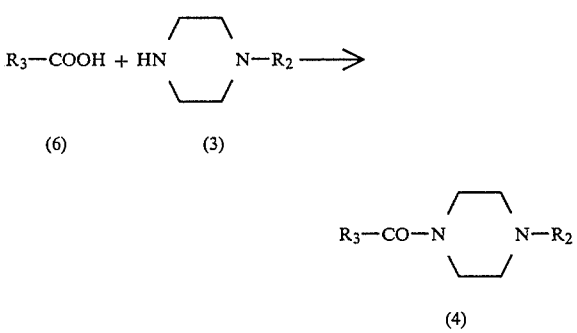

The reactive derivatives of carboxylic acid (6) include acyl halides such as acyl chlorides and acyl bromides; acyl azides; esters such as methyl ester, ethyl ester, and p-nitrophenyl ester; and acid anhydrides such as mixed acid anhydrides obtained by reacting methyl chlorocarbonate or ethyl chlorocarbonate with a carboxylic acid (6). It is possible to use without isolation the reactive derivative of a carboxylic acid (6) in the condensation with a piperazine derivative (3). It is also possible to use the acylpiperazine derivative (6) formed by the condensation directly, without isolation, in the subsequent reduction reaction.

The compound (1) of this invention formed by the method A or B can be isolated and purified by the customary means such as extraction, recrystallization, and column chromatography. The salt of the compound (1) is prepared also by the customary chemical procedure.

The piperazine derivative of this invention is used as an analgesic agent usually in a daily dose of about 0.5 to about 1,000 mg, in terms of purified compound of the formula (1), for the adult, which is administered preferably in two or three single doses. The dosage should be suitably adjusted, in particular cases, depending on the clinical features and age of the patient. The active ingredient content of the analgesic composition of this invention is suitably selected from the range of generally about 0.1 to about 1,000 mg, preferably 0.2 to 500 mg or thereabout, per single dose.

The analgesic agent of this invention is administered in various forms such as oral preparations, injections, suppositories for rectal application, and external preparations.

The analgesic agent of this invention is prescribed for medical application as a composition containing any of the customary carriers or excipients and compounded in a customary manner.

Oral preparations of the analgesic composition of this invention, such as tablets, capsules, granules and powders may contain excipients generally used in the art, such as, for example, calcium carbonate, calcium phosphate, starch, cane sugar, lactose, talc, magnesium stearate, gelatin, polyvinylpyrrolidone, gum arabic, sorbit, microcrystalline cellulose, polyethylene glycol, carboxymethylcellulose, silica, polyvinylacetal diethylaminoacetate, hydroxypropylmethylcellulose, and shellac. The tablets may be coated by a method well known to the art.

The liquid preparations of the present composition for oral administration include suspensions, solutions, syrups elixirs, and others in water or oil, which are prescribed in a generally known manner.

Injections of the present composition are suspensions and solutions in water or oil, or filled powders and lyophilized powders which are dissolved before use. The injections are prepared in an ordinary manner.

The present composition for suppositories for rectal application may contain those compounding excipients which are well known to the art, such as, for example, polyethylene glycol, lanolin, cacao butter, and fatty acid triglycerides.

The external preparations of the present composition are applied in the form of ointment or cream prepared by incorporating the active ingredient of this invention in a base or the like in a customary manner.

The invention is further illustrated below with reference to examples of synthesis and preparations as well as results of tests for analgesic activity and acute toxicity among pharmacological tests.

Examples of synthesis of piperazine derivatives of this invention by the method A and B are shown below. Characteristics of the piperazine derivatives obtained in these Examples and in other experiments conducted similarly to these Examples are as shown in Table 1.

EXAMPLES OF SYNTHESIS BY METHOD A

Example 1 (Synthesis of compound No. 2 in Table 1)

To 50 ml of ethanol, are added 3.6 g (0.02 mole) of 1-(4-fluorophenyl)piperazine, 2.0 g (0.022 mole) of cyclopropylmethyl chloride, and 1.9 g (0.023 mole) of sodium bicarbonate. The mixture is kept refluxing for 7 hours while being stirred. After having been cooled, the reaction mixture is freed from inorganic matters by filtration and the filtrate is concentrated in vacuo. The residue is dissolved in diethyl ether and gaseous hydrogen chloride is introduced into the solution, while being cooled, to precipitate crystals which are collected by filtration. Upon recrystallization from ethanol there are obtained 4.7 g (77% yield) of 1-(cyclopropylmethyl)-4-(4-fluorophenyl)piperazine dihydrochloride melting at 153°–154° C.

Example 2 (Synthesis of compound No. 12 in Table 1)

A mixture of 2.3 g (0.01 mole) of 1-(3-trifluoromethylphenyl)piperazine, 1.3 g (0.01 mole) of isopropyl bromide, 1.3 g of sodium bicarbonate and 25 ml of N,N-dimethylformamide is kept refluxing for 5 hours. After cooling and removal of inorganic matters by filtration, the filtrate is concentrated in vacuo. The residue is dissolved in diethyl ether. While cooling, gaseous hydrogen chloride is introduced into the ether solution and the precipitated crystals are collected by filtration. The crystals are recrystallized from methanol to yield 2.8 g (81% yield) of 1-(3-trifluoromethyl)-4-isopropylpiperazine dihydrochloride having a melting point of 179°–180° C.

Example 3 (Synthesis of compound No. 14 in Table 1)

1-Allyl-4-(3-trifluoromethylphenyl)piperazine dihydrochloride is obtained in a yield of 80% by allowing 1-(3-trifluoromethylphenyl)piperazine and allyl bromide to react in a manner similar to that in Example 2.

EXAMPLE OF SYNTHESIS BY METHOD B

Example 4 (Synthesis of compound No. 6 in Table 1)

In 40 ml of dichloromethane, are dissolved 2.3 g (0.01 mole) of 1-(3-trifluoromethylphenyl)piperazine and 1.0 g (0.01 mole) of triethylamine. To the resulting solution, while being cooled and stirred, is added dropwise a solution of 1.05 g (0.01 mole) of cyclopropanecarbonyl chloride in 10 ml of dichloromethane. The mixture is allowed to react at room temperature for 3 hours. The reaction mixture is washed successively with water, dilute hydrochloric acid and water, then dried over anhydrous sodium sulfate, and removed of the solvent by distillation to obtain oily 1-(cyclopropanecarbonyl)-4-(3-trifluoromethylphenyl)piperazine.

To 0.38 g (0.01 mole) of lithium aluminum hydride in 50 ml of tetrahydrofuran, is added dropwise with stirring a solution of the above 1-(cyclopropanecarbonyl)-4-(3-trifluoromethylphenyl)piperazine in 20 ml of tetrahydrofuran. After completion of the dropwise addition, the mixture is refluxed with stirring for 7 hours, then cooled, admixed with water and a dilute aqueous sodium hydroxide solution, and concentrated in vacuo. The residue is extracted with ether and dried over anhydrous sodium sulfate. Dry gaseous hydrogen chloride is introduced into the dried solution while being cooled in ice. The precipitated crystals are collected by filtration and recrystallized from ethanol to obtain 2.8 g (78% yield) of 1-(cyclopropylmethyl)-4-(3-trifluoromethylphenyl)piperazine dihydrochloride having a melting point of 172°–173° C.

TABLE 1

$$R_1-N\underset{\underset{}{\diagdown\_\_\_\diagup}}{\overset{\overset{}{\diagup\overline{\phantom{aa}}\diagdown}}{\phantom{aaaaa}}}N-R_2$$

| Compound No. | $R_1$ | $R_2$ | Type of salt | Melting point (°C.) | Molecular formula | Elementary analysis (%) Calculated (Found) | | |
|---|---|---|---|---|---|---|---|---|
| | | | | | | C | H | N |
| 1 | —CH₂—△ | 2-F-phenyl | Hydrochloride | 197–200 | $C_{14}H_{19}FN_2 \cdot 2HCl$ | 54.73 (54.44) | 6.89 (6.79) | 9.12 (9.50) |
| 2 | " | 4-F-phenyl | " | 153–154 | $C_{14}H_{19}FN_2 \cdot 2HCl$ | 54.73 (54.47) | 6.89 (6.62) | 9.12 (9.37) |
| 3 | " | 3-Cl-phenyl | " | 183–186 | $C_{14}H_{19}ClN_2 \cdot 2HCl$ | 51.95 (52.33) | 6.54 (6.68) | 8.65 (8.99) |
| 4 | " | 4-Cl-phenyl | " | 180.5–182.5 | $C_{14}H_{19}ClN_2 \cdot 2HCl$ | 51.95 (52.06) | 6.54 (6.71) | 8.65 (8.84) |
| 5 | " | 3,4-diCl-phenyl | " | 190 (decomp.) | $C_{14}H_{18}Cl_2N_2 \cdot 2HCl$ | 46.95 (47.31) | 5.63 (6.02) | 7.82 (8.22) |
| 6 | " | 3-CF₃-phenyl | " | 172–173 | $C_{15}H_{19}F_3N_2 \cdot 2HCl$ | 50.43 (50.58) | 5.93 (5.95) | 7.84 (8.02) |
| 7 | " | 3-CF₃-phenyl | Oxalate | 164–165 | $C_{15}H_{19}F_3N_2 \cdot C_2H_2O_4$ | 54.54 (54.92) | 5.65 (5.79) | 7.48 (7.82) |
| 8 | " | 3-CF₃-phenyl | Maleate | 156–158 | $C_{15}H_{19}F_3N_2 \cdot C_4H_4O_4$ | 59.37 (59.67) | 6.03 (6.15) | 7.29 (7.40) |
| 9 | " | 3-CF₃-phenyl | Tartarate | 45–50 | $C_{15}H_{19}F_3N_2 \cdot C_4H_6O_6$ | 52.53 (52.33) | 5.80 (6.32) | 6.45 (6.60) |
| 10 | " | 3-CF₃-phenyl | Citrate | 105–107 | $C_{15}H_{19}F_3N_2 \cdot C_6H_8O_7$ | 52.94 (53.05) | 5.71 (5.66) | 5.88 (6.17) |
| 11 | " | 2-CF₃-4-Cl-phenyl | Hydrochloride | 173–175 | $C_{15}H_{18}ClF_3N_2 \cdot HCl$ | 50.70 (50.61) | 5.39 (5.80) | 7.88 (7.92) |
| 12 | —CH(CH₃)₂ | 3-CF₃-phenyl | " | 179–180 | $C_{14}H_{19}F_3N_2 \cdot 2HCl$ | 48.71 (48.57) | 6.13 (6.19) | 8.11 (8.31) |
| 13 | " | 3-CF₃-phenyl | Citrate | 133–134 | $C_{14}H_{19}F_3N_2 \cdot C_6H_8O_7$ | 51.72 (51.82) | 6.03 (6.14) | 5.86 (5.76) |

TABLE 1-continued

| Compound No. | $R_1$ | $R_2$ | Type of salt | Melting point (°C.) | Molecular formula | Elementary analysis (%) Calculated (Found) | | |
| --- | --- | --- | --- | --- | --- | --- | --- | --- |
| | | | | | | C | H | N |
| 14 | —CH$_2$CH=CH$_2$ |  | Hydrochloride | 177–178 | C$_{14}$H$_{17}$F$_3$N$_2$.2HCl | 48.99 (49.02) | 5.58 (5.88) | 8.16 (8.40) |

PREPARATION EXAMPLE 1

Injections are prepared in a common manner according to the following recipe:

| | |
| --- | --- |
| 1-(Cyclopropylmethyl)-4-(3-trifluoromethylphenyl)piperazine dihydrochloride (Compound No. 6) | 5 mg |
| Physiological saline to make up 2 ml per ampul. | |

PREPARATION EXAMPLE 2

Tablets are prepared in a common manner according to the following recipe:

| | |
| --- | --- |
| 1-(Cyclopropylmethyl)-4-(3-trifluoromethylphenyl)piperazine dihydrochloride (Compound No. 6) | 50 mg |
| Lactose | 85 |
| Crystalline cellulose | 50 |
| Hydroxypropylstarch | 30 |
| Talc | 4 |
| Magnesium stearate | 1 |
| Total | 220 mg/tablet |

PREPARATION EXAMPLE 3

Capsules are prepared in an ordinary manner according to the following recipe:

| | |
| --- | --- |
| 1-(Cyclopropylmethyl)-4-(3-trifluoromethylphenyl)piperazine dihydrochloride (Compound No. 6) | 100 mg |
| Lactose | 50 |
| Potato starch | 50 |
| Crystalline cellulose | 109 |
| Magnesium stearate | 1 |
| Total | 310 mg per capsule |

PREPARATION EXAMPLE 4

Suppositories are prepared in an ordinary manner according to the following recipe:

| | |
| --- | --- |
| 1-(Cyclopropylmethyl)-4-(3-trifluoromethylphenyl)piperazine citrate (Compound No. 10) | 250 mg |
| Witepzol W-35 (Trademark for Dynamit Nobel Co.) | 750 |
| Total | 1,000 mg per suppository |

PREPARATION EXAMPLE 5

Granules are prepared in an ordinary manner according to the following recipe:

| | |
| --- | --- |
| 1-(Cyclopropylmethyl)-4-(3-trifluoromethylphenyl)piperazine citrate (Compound No. 10) | 200 mg |
| Lactose | 500 |
| Corn starch | 280 |
| Hydroxypropylcellulose | 20 |
| Total | 1,000 mg per envelope |

PHARMACOLOGICAL TEST

The results of analgesic activity test and acute toxicity test performed on the compounds of this invention and aminopyrin as control are as described below. The results of test for representative compounds are summarized in Table 2.

1. ANALGESIC ACTIVITY TEST (1) Acetic acid-induced stretching method

Groups of each 10 dd strain male mice (about 18 g in body weight) were used for the test. Each mouse was orally administered with the drug being tested. Thirty minutes after the administration, 0.1 ml/10 g of a 0.6% acetic acid solution was intraperitoneally injected. After 25 minutes from the injection of acetic acid, the stretching symptom was observed for 5 minutes. The percentage effectiveness was determined by the formula $$\text{Percentage effectiveness} = \frac{\text{Number of animals without symptom}}{\text{Number of test animals}} \times 100$$

From the effectiveness data, the median effective dose (ED$_{50}$) and its 95% confidence limits were calculated by the method of Litchfield-Wilcoxon.

(2) Modified Haffner method

Groups of each 10 dd strain male mice (about 19 g in body weight) were used for the test. Thirty minutes after the oral administration of the drug under test, 2 mg/kg of morphine hydrochloride was subcutaneously injected. After 15 minutes, the basal part of the mouse tail was clamped with Kocher's forceps four times at each time interval of 15 minutes to observe the pain reaction of each mouse. The percentage effectiveness was calculated by the formula $$\text{Percentage effectiveness} = \frac{\text{Number of mice without pain reaction}}{\text{Number of test animals}} \times 100$$

From the effectiveness data, the median effective dose (ED$_{50}$) and its 95% confidence limits were calculated by the method of Litchfield-Wilcoxon.

2. ACUTE TOXICITY TEST

Groups of each 4-6 dd strain male mice (about 19 g in body weight) were used for the test. The mice were observed for 72 hours after the oral administration of the drug under test. The median lethal dose (LD$_{50}$) and its 95% confidence limits were calculated from the mortality in 72 hours of observation. When the median lethal dose was not obtainable, the dose (mg/kg) and the ratio (number of dead animals)/(number of test animals) were shown in Table 2.

TABLE 2

| Compound No. | Analgesic activity, ED$_{50}$ (mg/kg) | | Acute toxicity, LD$_{50}$ (mg/kg) or | |
|---|---|---|---|---|
| | Acetic acid stretching method | Hoffner method | Dose (mg/kg) | Number of dead animals / Number of test animals |
| 1 | 12.6 (6.4–24.8) | 11.0 (4.8–25.2) | 250 500 100 | 2/6 3/6 6/6 |
| 2 | 9.4 (4.9–18.0) | 13.2 (9.6–18.2) | 250 500 1000 | 1/6 5/6 6/6 |
| 3 | | 13.8 (9.5–20.0) | 250 500 1000 | 0/6 2/6 6/6 |
| 4 | 17.9 (8.3–38.5) | 6.3 (3.8–10.4) | 250 500 1000 | 0/6 5/6 6/6 |
| 5 | 17.2 (8.1–36.5) | 7.2 (4.3–12.0) | 250 500 1000 | 0/6 2/6 6/6 |
| 6 | 2.8 (1.7–4.6) | 3.7 (2.2–6.0) | 250 500 1000 | 0/6 4/6 6/6 |
| 7 | | 5.5 (3.1–9.6) | 250 500 1000 | 0/6 2/6 6/6 |
| 9 | | 4.9 (2.3–10.2) | 250 500 1000 | 0/6 3/6 6/6 |
| 10 | 8.7 (4.6–16.4) | 2.5 (1.2–5.4) | 250 500 1000 | 0/6 2/6 6/6 |
| 11 | 20.2 (12.1–33.7) | 5.8 (4.1–8.3) | 250 500 1000 | 0/6 5/6 6/6 |
| 12 | 4.2 (2.6–6.8) | 4.9 (3.4–7.1) | 250 500 1000 | 0/6 6/6 6/6 |
| 14 | 13.6 (6.2–29.9) | 7.0 (4.2–11.6) | 250 500 1000 | 0/6 4/6 6/6 |
| Aminopyrin | 63.0 (44.7–88.8) | 65.0 (45.8–92.3) | 750 | (74.1–75.9) |

What is claimed is:

1. A piperazine compound having the formula (1),

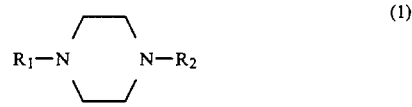

wherein R$_1$ represents cyclopropylmethyl, isopropyl, or allyl and R$_2$ represents phenyl substituted by one or two halogen atoms and/or one trifluoromethyl group, or pharmaceutically acceptable salts thereof.

2. A piperazine compound according to claim 1, wherein R$_2$ is phenyl having a trifluoromethyl substituent.

3. 1-(Cyclopropylmethyl)-4-(2-fluorophenyl)piperazine dihydrochloride.

4. 1-(Cyclopropylmethyl)-4-(4-fluorophenyl)piperazine dihydrochloride.

5. 1-(Cyclopropylmethyl)-4-(3-chlorophenyl)piperazine dihydrochloride.

6. 1-(Cyclopropylmethyl)-4-(4-chlorophenyl)piperazine dihydrochloride.

7. 1-(Cyclopropylmethyl)-4-(3,4-dichlorophenyl)piperazine dihydrochloride.

8. 1-(Cyclopropylmethyl)-4-(3-trifluoromethylphenyl)piperazine dihydrochloride.

9. 1-(Cyclopropylmethyl)-4-(3-trifluoromethylphenyl)piperazine oxalate.

10. 1-(Cyclopropylmethyl)-4-(3-trifluoromethylphenyl)piperazine maleate.

11. 1-(Cyclopropylmethyl)-4-(3-trifluoromethylphenyl)piperazine tartarate.

12. 1-(Cyclopropylmethyl)-4-(3-trifluoromethylphenyl)piperazine citrate.

13. 1-(Cyclopropylmethyl)-4-(3-trifluoromethylphenyl)piperazine hydrochloride.

14. 1-Isopropyl-4-(3-trifluoromethylphenyl)piperazine dihydrochloride.

15. 1-Isopropyl-4-(3-trifluoromethylphenyl)piperazine citrate.

16. 1-Allyl-4-(3-trifluoromethylphenyl)piperazine dihydrochloride.

17. An analgesic composition comprising as active ingredient a pharmaceutically effective amount of a piperazine compound having the formula (1)

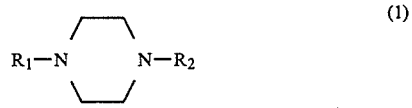

wherein R$_1$ represents cyclopropylmethyl, isopropyl, or allyl and R$_2$ represents phenyl substituted by one or two halogen atoms and/or one trifluoromethyl group, or a pharmaceutically acceptable salt thereof, and a pharmaceutically acceptable carrier therefor.

18. A method of producing an analgesic effect in a patient in need of such effect, said method comprising administering to said patient an effective amount of a compound of claim 1.

19. Method of claim 18, wherein about 0.1 to about 1000 mg of said compound is administered to said patient per single dose.

20. Method of claim 19, wherein said amount is about 0.2 to 500 mg.